US006541630B1

(12) United States Patent
Atherall et al.

(10) Patent No.: US 6,541,630 B1
(45) Date of Patent: Apr. 1, 2003

(54) FUNGICIDES

(75) Inventors: John Frederick Atherall, Saffron Walden (GB); Thomas Lawley Hough, Cambridge (GB); Stephen David Lindell, Frankfurt (DE); Mary Josephine O'Mahony, Cambridge (GB); John Henry Parsons, Saffron Walden (GB); Elizabeth Anne Saville-Stones, Cambridge (GB)

(73) Assignee: Agrevo UK Limited (GB)

( * ) Notice: Subject to any disclaimer, the term of this patent is extended or adjusted under 35 U.S.C. 154(b) by 0 days.

(21) Appl. No.: 10/172,891

(22) Filed: Jun. 13, 2002

Related U.S. Application Data

(62) Division of application No. 09/423,135, filed as application No. PCT/GB98/01286 on Nov. 5, 1999, now Pat. No. 6,432,964.

(30) Foreign Application Priority Data

| | | |
|---|---|---|
| May 8, 1997 | (GB) | 9709210 |
| Nov. 18, 1997 | (GB) | 9724328 |
| Nov. 26, 1997 | (GB) | 9724849 |
| Nov. 26, 1997 | (GB) | 9724852 |
| Nov. 26, 1997 | (GB) | 9724854 |

(51) Int. Cl.[7] .......... C07D 495/04
(52) U.S. Cl. .......... 544/278
(58) Field of Search .......... 544/278

(56) References Cited

FOREIGN PATENT DOCUMENTS

| | | |
|---|---|---|
| WO | 0665224 | 8/1995 |
| WO | 9702262 | 1/1997 |
| WO | 9733890 | 9/1997 |

*Primary Examiner*—John Ford
(74) *Attorney, Agent, or Firm*—Ostrolenk, Faber, Gerb & Soffen, LLP

(57) ABSTRACT

The invention provides the use in combating fungi of compounds of general formula I wherein $R^1$ is hydrogen, hydroxy, acyl, acyloxy, optionally substituted amino, $R^a$, $R^a{}_3Si$, $R^aS$ or $R^aO$, where $R^a$ is optionally substituted alkyl, optionally substituted alkenyl, optionally substituted alkynyl, optionally substituted cycloalkyl, optionally substituted cycloalkenyl, optionally substituted aryl or optionally substituted heterocyclyl; Z is oxygen or sulfur; M is a thiophene ring; and $R^3$ and $R^4$, which may be the same or different, have the same meaning as $R^a$ or can be optionally substituted amino, hydrogen, halogen, cyano, nitro or a group $OR^c$ or $S(O)_mR^c$, where $R^c$ has the same meaning as $R^a$ or is hydrogen or acyl and m is 0, 1 or 2; or $R^3$ and $R^4$ together with the atoms to which they are attached form an optionally substituted carbocyclic or heterocyclic ring; together with tautomers of compounds where $R^1$ is hydrogen.

(I)

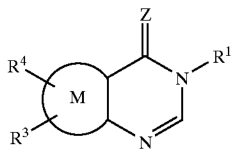

1 Claim, No Drawings

FUNGICIDES

CROSS REFERENCE TO RELATED APPLICATION

This is a divisional of U.S. patent application Ser. No. 09/423,135 filed Nov. 5, 1999 by John Frederick ATHERALL, Thomas Lawley HOUGH, Stephen David LINDELL, Mary Josephine O'MAHONY, John Henry PARSONS, and Elizabeth Anne SAVILLE-STONES entitled "FUNGICIDES", now U.S. Pat. No. 6,432,964, filed Aug. 13, 2002, which is, in turn, a 35 U.S.C. §371 national phase conversion of PCT/GB98/01286 filed May 1, 1998.

The invention relates to the use of compounds in combating fungi in plants.

In Bull. Soc. Chim. France, 1970, (10), 3630–6, there are disclosed certain thienopyrimidines. We have discovered that at least one of these compounds has utility in combating fungi.

In WO97/02262 there are diclosed thienopyrimidine derivatives, useful as fungicides, substituted at the 2-position by an oxygen, sulfur or nitrogen.

In EP0665224 there are disclosed two specific 2-benzyl substituted thienopyrimidines useful as fungicides and/or herbicides.

In WO99/14202, published after the priority date of this application, there are disclosed 2-substituted thienopyrimidines useful as fungicides.

The invention provides the use in combating fungi of compounds of general formula I (I)

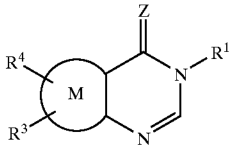

wherein $R^1$ is hydrogen, hydroxy, acyl, acyloxy, optionally substituted amino, $R^a$, $R^a{}_3Si$, $R^aS$ or $R^aO$, where $R^a$ is optionally substituted alkyl, optionally substituted alkenyl, optionally substituted alkynyl, optionally substituted cycloalkyl, optionally substituted cycloalkenyl, optionally substituted aryl or optionally substituted heterocyclyl;

Z is oxygen or sulfur;

M is a thiophene ring; and $R^3$ and $R^4$, which may be the same or different, have have the same meaning as $R^a$ or can be optionally substituted amino, hydrogen, halogen, cyano, nitro or a group $OR^c$ or $S(O)_mR^c$, where $R^c$ has the same meaning as $R^a$ or is hydrogen or acyl and m is 0, 1 or 2; or $R^3$ and $R^4$ together with the atoms to which they are attached form an optionally substituted carbocyclic or heterocyclic ring;

together with tautomers of compounds where $R^1$ is hydrogen.

Most of the above compounds are novel, and accordingly the invention includes any novel compounds of formula 1 as defined above, including in particular, 7-bromo-3-methyl-3,4-dihydrothieno[3,2-d]pyrimidin-4-one.

Any alkyl group present in the molecule is preferably of 1 to 10 carbon atoms, especially of 1 to 7 carbon atoms, and particularly of 1 to 5 carbon atoms.

Any alkenyl or alkynyl group present in the molecule is preferably of 2 to 7 carbon atoms, for example allyl, vinyl or propargyl.

Any cycloalkyl, cycloalkenyl or cycloalkynyl group present in the molecule is preferably of 3 to 7 carbon atoms, especially cyclopropyl, cyclopentyl, cyclohexyl or cyclohexenyl.

Substituents, when present on any alkyl, alkenyl, alkynyl, cycloalkyl, cycloalkenyl cycloalkynyl moiety may for example be halogen, cyano, optionally substituted alkoxy, optionally substituted alkylthio, mercapto, hydroxy, nitro, optionally substituted amino, acyl, acyloxy, acylthio, optionally substituted phenyl, optionally substituted heterocyclyl, optionally substituted phenylthio, optionally substituted phenoxy, optionally substituted heterocyclyloxy, optionally substituted heterocyclylthio.

Cycloalkyl, cycloalkenyl, cycloalkynyl groups may also be substituted by optionally substituted alkyl, alkynyl or alkenyl and vice versa.

Substituents when present on any phenyl or heterocyclyl group may be the same or different and include $R^a$-$(X)_n$-, (where $R^a$ is as defined above, X is oxygen or sulfur and n is 0 or 1), optionally substituted amino, hydroxy, halogen, cyano, nitro, acyl, or two adjacent groups together with the carbon atoms to which they are attached can form an optionally substituted benzo or heterocyclic ring. Heterocyclyl groups may also be substituted by double-bonded substituents such as oxo or imino.

The term heterocyclyl includes both aromatic and non-aromatic heterocyclyl groups. Heterocyclyl groups are generally 5, 6 or 7-membered rings containing up to 4 hetero atoms selected from nitrogen, oxygen and sulfur. Examples of heterocyclyl groups are furyl, thienyl, pyrrolyl, pyrrolinyl, pyrrolidinyl, imidazolyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridyl, piperidinyl, dioxanyl, morpholino, dithianyl, thiomorpholino, pyridazinyl, pyrimidinyl, pyrazinyl, piperazinyl, triazinyl, thiazolinyl, benzimidazolyl, tetrazolyl, benzoxazolyl, imidazopyridinyl, 1,3-benzoxazinyl, 1,3-benzothiazinyl, oxazolopyridinyl, benzofuranyl, quinolinyl, quinazolinyl, quinoxalinyl, sulfolanyl, dihydroquinazolinyl, benzothiazolyl, phthalimido, benzofuranyl, azepinyl, oxazepinyl, thiazepinyl, tetrahydrofuryl, diazepinyl and benzodiazepinyl.

Amino groups may be substituted for example by one or two $R^1$ groups, or two substituents can form a ring, preferably a 5 to 7-membered ring, which may be substituted and may contain other heteroatoms, for example morpholine, thiomorpholine, or piperidine. This ring can be substituted as for heterocyclyl.

The term acyl includes the residue of sulfur and phosphorus-containing acids as well as carboxylic acids. Examples of acyl groups are thus $-COR^5$, $-COOR^5$, $-CXNR^5R^6$, $-CON(R^5)OR^6$, $-COONR^5R^6$, $-CON(R^5)NR^6R^7$, $-COSR^5$, $-CSSR^5$, $-S(O)_pR^5$, $-S(O)_2OR^5$, $-S(O)_p NR^5R^6$, $-P(=X)(OR^5)(OR^6)$, $-CO-COOR^5$, where $R^5$, $R^6$ and $R^7$, which may be the same or different, are hydrogen, optionally substituted alkyl, optionally substituted cycloalkyl, optionally substituted cycloalkenyl, optionally substituted alkenyl, optionally substituted alkynyl, optionally substituted phenyl or optionally substituted heterocyclyl, or $R^5$ and $R^6$, or $R^6$ and $R^7$, together with the atom(s) to which they are attached can form a ring, p is 1 or 2 and X is O or S.

We have found that compounds of the invention wherein Z is oxygen are particularly effective in combating fungi.

Preferred $R^1$ groups are hydrogen, 2l-oxotetrahydrofuranyl or optionally substituted alkyl. In particular when $R^1$ is optionally substituted alkyl we have found $C_1$–$C_5$ alkyl groups. e.g. methyl, to be especially preferred. Preferred substituents are alkoxycarbonyl, alkanoyloxy, cyano and phenyl, itself optionally substituted by alkyl, alkoxy, haloalkyl or halogen.

$R^3$ and $R^4$ can be the same or different and are preferably hydrogen, halogen or optionally substituted alkyl, it is generally desirable that one of $R^3$ or $R^4$, is halogen, especially bromine or chlorine, and particularly bromine, and the other it hydrogen. In particular when $R^3$ or $R^4$ is optionally substituted alkyl, we have found $C_1$–$C_5$ alkyl groups, especially tert.-butyl, to be most active. When $R^3$ or $R^4$ is substituted alkyl, preferred substituents are halogen, e.g. trifluoromethyl.

Although good activity has been shown for each fused ring system, generally the thieno[3,2-d]pyrimidine ring system is preferred.

The compounds of the invention have activity as fungicides, especially against fungal diseases of plants, e.g. mildews and particularly cereal powdery mildew (*Erysiphe graminis*) and vine downy mildew (*Plasmopara viticola*), rice blast (*Pyricularia oryzae*), cereal eyespot (*Pseudocercosporella herpotrichoides*), rice sheath blight (*Pellicularia sasakii*), grey mould (*Botrytis cinerea*), damping off (*Rhizoctonia solani*), wheat brown rust (*Puccinia recondita*), late tomator or potato blight (*Phytophthora infestans*), apple scab (*Venturia inaequalis*), glume blotch (*Leptosphaeria nodorum*). Other fungi against which the compounds may be active include other powdery mildews, other rusts, and general pathogens of Deuteromycete, Ascomycete, Phycomycete and Basidiomycete origin.

The invention thus also provides a method of combating fungi at a locus infested or liable to be infested therewith, which comprises applying to the locus a compound of formula I.

The invention also provides an agricultural composition comprising a compound of formula I in admixture with an agriculturally acceptable diluent or carrier.

The composition of the invention may of course include more than one compound of the invention.

In addition, the composition can comprise one or more additional active ingredients, for example compounds known to possess plant-growth regulant, herbicidal, fungicidal, insecticidal or acaricidal properties. Alternatively the compound of the invention can be used in sequence with the other active ingredient.

The diluent or carrier in the composition of the invention can be a solid or a liquid optionally in association with a surface-active agent, for example a dispersing agent, emulsifying agent or wetting agent. Suitable surface-active agent include anionic compounds such as a carboxylate, for example a metal carboxylate of a long chain fatty acid; an N-acylsarcosinate; mono- or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl-aryl sulfonates such as alkyl-benzene sulfonates or lower alkylnaphthalene sulfonates, e.g. butyl-naphthalene sulfonate; salts of sulfonated naphthalene-formaldehyde condensates; salts of sulfonated phenol-formaldehyde condensates; or more complex sulfonates such as the amide sulfonates, e.g. the sulfonated condensation product of oleic acid and N-methyl taurine or the dialkyl sulfosuccinates, e.g. the sodium sulfonate of dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g. sorbitan fatty acid esters, condensation products of such esters with ethylene oxide, e.g. poloxyethylene sorbitan fatty acid esters, block copolymers of ethylene oxide and propylene oxide, acetylenic glycols such as 2,4,7,9-tetramethyl-5-decyne-4,7-diol, or ethoxylated acetylenic glycols.

Examples of a cationic surface-active agent include, for instance, an aliphatic mono-, di-, or polyamine as an acetate, naphthenate or oleate; an oxygen-containing amine such as an amine oxide or poloxyethylene alkylamine; an amine-linked amine prepared by the condenstaion of a carboxylic acid with a di- or polyamine; or a quaternary ammonium salt.

The compositions of the invention can take any form known in the art for the formulation of agrochemicals for example, a solution, a dispersion, an aqueous emulsion, a dusting powder, a seed dressing, a fumigant, a smoke, a dispersible powder, and emulsifiable concentrate or granules. Moreover it can be in a suitable form for direct application or as a concentrate or primary composition which requires dilution with a suitable quantity of water or other diluent before application.

An emulsifiable concentrate comprises a compound of the invention dissolved in a water-immiscible solvent which is formed into an emulsion with water in the presence of an emulsifying agent.

A dusting powder comprises a compound of the invention intimately mixed and ground with a solid pulverulent diluent, for example, kaolin.

A granular solid comprises a compound of the invention associated with similar diluents to those which may be employed in dusting powders, but the mixture is granulated by known methods. Alternatively it comprises the active ingredient absorbed or adsorbed on a pre-granular diluent, for example, Fuller's earth, attapulgite or limestone grit.

Wettable powders, granules or grains usually comprise the active ingredient in admixture with a suitable surfactant and an inert powder diluent such as china clay.

Another suitable concentrate is a flowable suspension concentrate which is formed by grinding the compound with water or other liquid, a wetting agent and a suspending agent.

The concentration of the active ingredient in the composition of the present invention, as applied to plants is preferably within the range of 0.0001 to 1.0 per cent by weight, especially 0.0001 to 0.01 per cent by weight. In a primary composition, the amount of active ingredient can vary widely and can be, for example, from 5 to 95 per cent by weight of the composition.

In the method of the invention, the compound is generally applied to seeds, plants or their habitat. Thus, the compound can be applied directly to the soil before, at or after drilling so that the presence of active compound in the soild can control the growth of fungi which may attack seeds. When the soil is treated directly the active compound can be applied in any manner which allows it to be intimately mixed with the soil such as by spraying, by broadcasting a solid form or granules, or by applying the active ingredient at the same time as drilling by inserting it in the same drill as the seeds. A suitable application rate is within the range of from 5 to 1000 g per hectare, more preferably from 10 to 500 g per hectare.

Alternatively, the active compound can be applied directly to the plant by, for example, spraying or dusting either at the time when the fungus has begun to appear on the plant or before the appearance of fungus as a protective measure. In both such cases the preferred mode of application is by foliar spraying. It is generally important to obtain good control to fungi in the early stages of plant growth as this is the time when the plant can be most severely damaged. The spray or dust can conveniently contain a pre- or post-emergence herbicide if this is thought necessary. Sometimes, it is practicable to treat the roots of a plant before or during planting, for example, by dipping the roots in a suitable liquid or solid composition. When the active compound is applied directly to the plant a suitable rate of application is from 0.025 to 5 kg per hectare, preferably from 0.05 to 1 kg per hectare.

In addition, the compounds of the invention can be applied to plants, or parts thereof, which have been genetically modified to exhibit a trait such as fungal and/or herbicidal resistance.

The general formula I covers thieno[3,2-d]pyrimidine derivatives II, thieno[3,4-d]pyrimidine derivatives III, and thieno[2,3-d]pyrimidine derivatives IV.

(II)

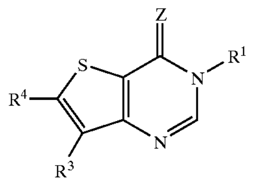

[3, 2-d]

(III)

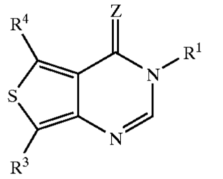

[3, 4-d]

(IV)

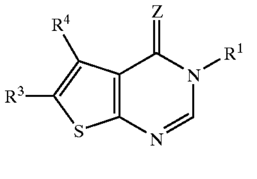

[2, 3-d]

Compounds of formula IId, i.e. compounds of general formula II where $R^1$ is hydrogen and Z is oxygen, can be prepared from compound V in two steps according to reaction Scheme 1. compounds of formula V may be prepared by a number a methods: see for example references and reviews in Comprehensive Heterocyclic Chemistry. Eds Katritsky AR and Rees C. W. (4), 863–934 and Comprehensive Heterocyclic Chemistry II, Eds Katritzky A. R. Rees C. W. and Scriven E. F. V. (2) 607–678.

Scheme 1

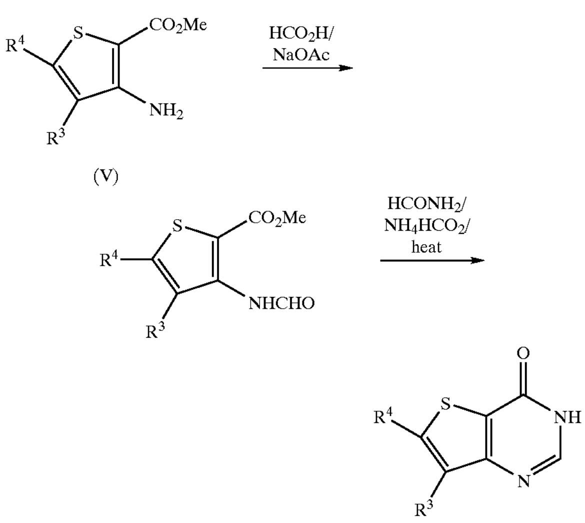

(V)

(IIc)

Equivalent compounds of general formula III and IV can be made mutatis mutandis in similar manner.

Compounds of formula IId, i.e. compounds of general formula II where $R^1$ is hydrogen, Z is oxygen, $R^3$ is a group inert to lithium diisopropylamide and $R^4$ is a substituent E, can be prepared in four steps from IIe according to reaction Scheme 2 wherein E is introduced using electrophilic substitution. Reaction conditions for introducing substituent E involve treatment of intermediate VIII with lithium diisopropylamide followed by addition of a suitable electrophile source. For example when E is -CH(R)OH, CH, bromine or methyl, the electrophile source is respectively, RC(=O)H, tosyl cyanide, N-bromosuccinimide or methyl iodide. When the group E is -CH(R)OH, elimination of water may occur to form the corresponding compound II where E is alkenyl.

Scheme 2

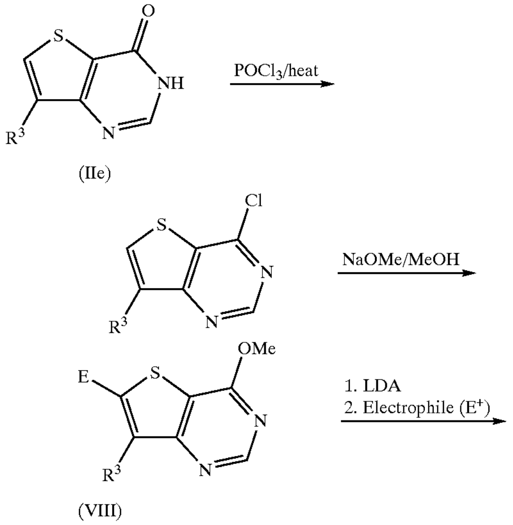

(IIe)

(VIII)

-continued

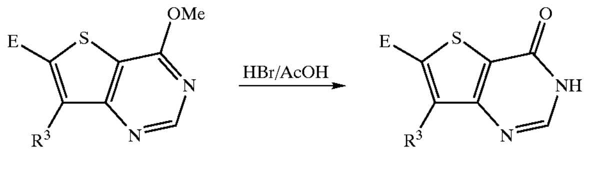

(IId) (IId)

Compounds of formula IIf, i.e. compounds of formula II where $R^1$ is hydrogen and Z is sulfur can, be made in two steps from IIa, by reaction with phosphorus oxychloride followed by treatment with sodium hydrosulfide according to reaction Scheme 3.

Scheme 3

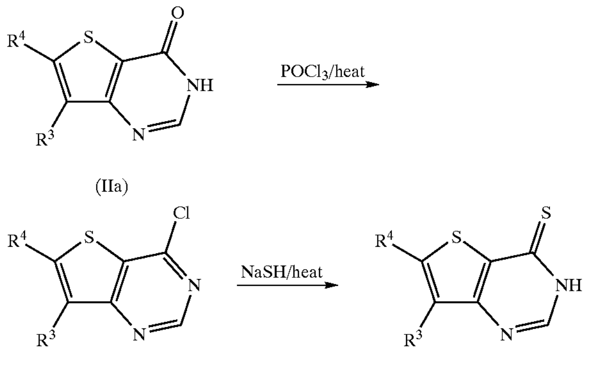

(IIa)

(IIf)

Equivalent compounds of general formula III and IV can be made mutatis mutandis in similar manner.

Compounds of formula IIg, i.e. compounds of general formula II where $R^3$ is a halogen, can be prepared according to reaction Scheme 4. When the halogen is bromine or chlorine, preferred reaction conditions comprise reacting IIh with bromine or chlorine in glacial acetic acid.

Scheme 4

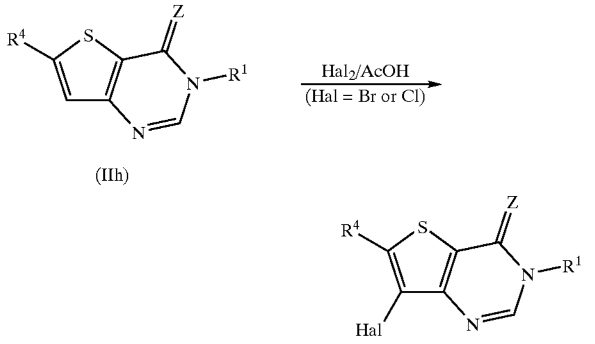

(IIh)

(IIg)

Compounds of formula IIb, i.e. compounds of formula II where Z is oxygen, can be prepared from compounds of formula IIa, i.e. compounds of formula II where Z is oxygen and $R^1$ is hydrogen, by reacting IIa with base followed by treatment with $R^1X$ where x is a leaving group. For example when $R^1$ is alkyl, preferred reaction conditions comprise treating IIa with sodium hydride followed by an alkyl iodide (Scheme 5).

Scheme 5

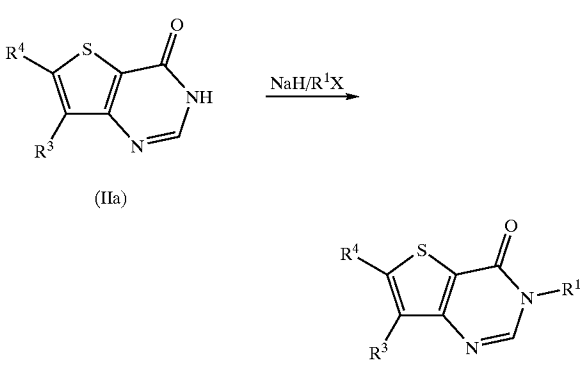

(IIa)

(IIb)

Equivalent compounds of general formula III and IV can be made mutatis mutandis in similar manner.

Compounds of formula IIi, i.e. compounds of formula II where $R^1$ is hydroxy and Z is oxygen, may be prepared in three steps starting from compound V according to reaction Scheme 6.

Scheme 6

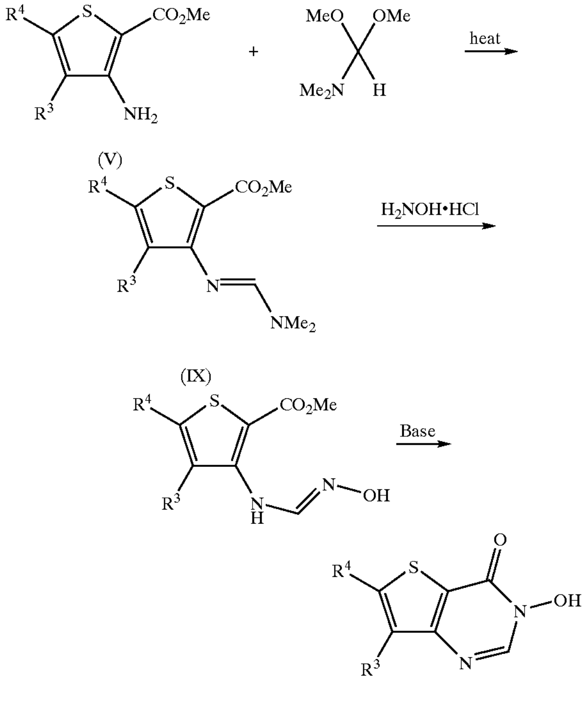

(V)

(IX)

(IIi)

Equivalent compounds of general formula III and IV can be made mutatis mutandis in similiar manner.

Compounds of formula IIj, i.e. compounds of formula II where $R^1$ is $R''O$, may be prepared according to Scheme 7 by reacting compounds of formula IIk, with a suitable base, preferably sodium hydride followed by $R''X$, where X is a leaving group.

Scheme 7

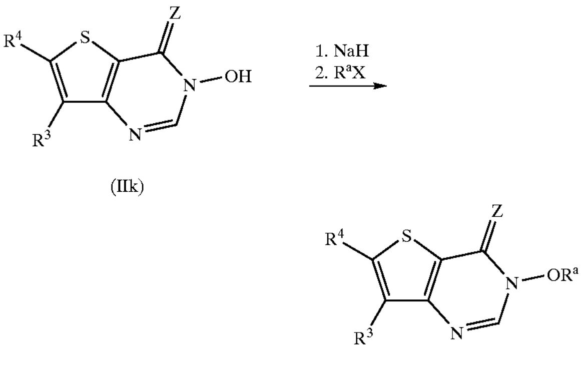

(IIk)

(IIj)

Equivalent compound of general formula III and IV can be made mutatis mutandis in similar manner.

Compounds of formula IIm, i.e. compounds of formula II where $R^1$ is acyloxy, may be prepared according to Scheme 8 by reacting compounds of formula IIk with the corresponding acyl chloride.

Scheme 8

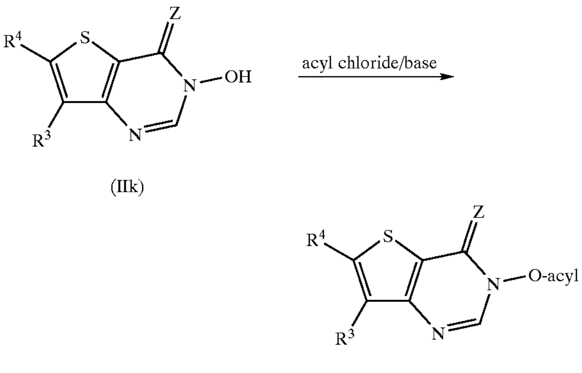

(IIk)

(IIm)

Equivalent compounds of general formula III and IV can be made mutatis mutandis in similar manner.

Compounds of formula IIn, i.e. compounds of general formula II where $R^1$ is $NH_2$ and Z is oxygen, can be prepared by reacting compounds of formula IX with hydrazine hydrochloride according to reaction Scheme 9. See Scheme 6 for the preparation of IX.

Scheme 9

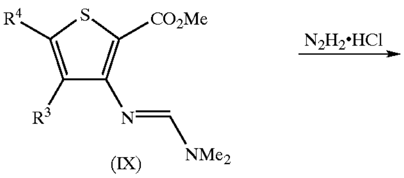

(IX)

-continued

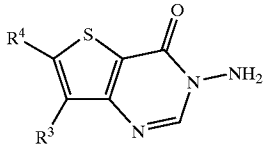

(IIn)

Equivalent compounds of general formula III and IV can be made mutatis mutandis in similar manner.

Compounds of formula IIp, i.e. compounds of general formula II where $R^1$ is NH-acyl, can be prepared by reacting compounds of formula IIq with the corresponding acyl halide according to reaction Scheme 10.

Scheme 10

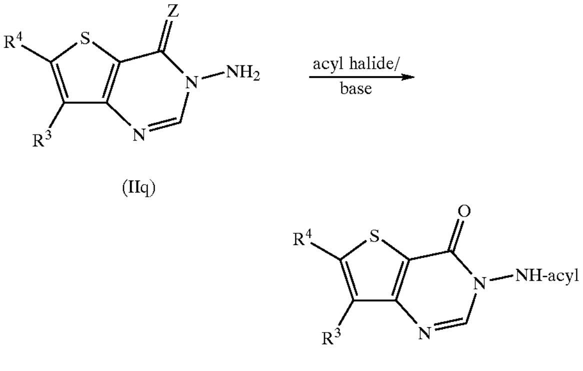

(IIq)

(IIp)

Equivalent compounds of general formula III and IV can be made mutatis mutandis in similar manner.

Compounds of formula IIr, i.e. compounds of general formula II where $R^1$ is -N═CHR and Z is oxygen, can be prepared according to reaction Scheme 11. R is preferably an aromatic group and $R^d$ is preferably a lower alkyl group.

Scheme 11

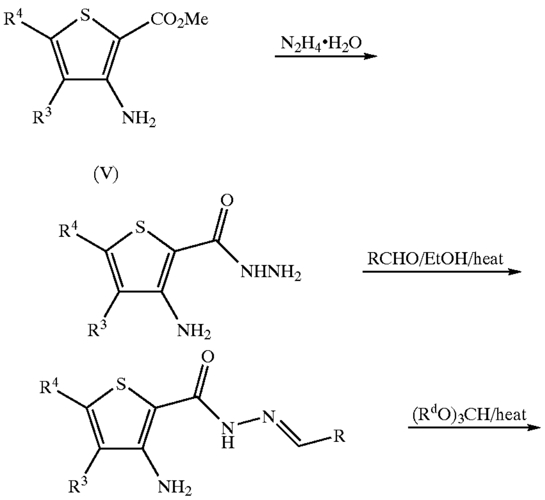

(V)

-continued

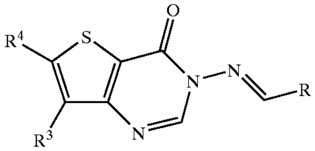

(IIr)

Equivalent compounds of general formula III and IV can be made mutatis mutandis in similar manner.

Compounds of IIs, i.e. compounds of general formula III where $R^3$ is bromine, can be prepared by treating compound of formula IIt with bromine in glacial acetic acid heated under reflux for 2 hours. Continued heating for 5 hours gives the dibrominated compound IIIu, where $R^3$ and $R^4$ are both bromine (Scheme 12).

Scheme 12

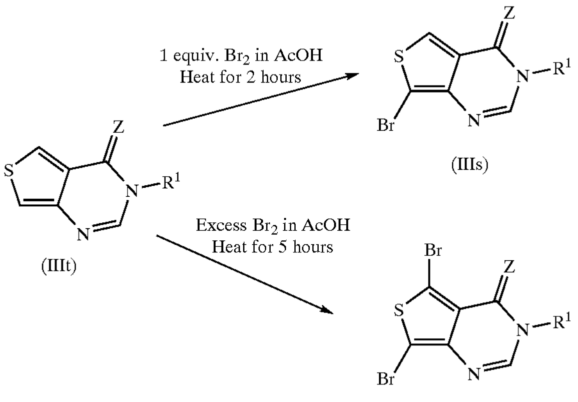

(IIIs)

(IIIt)

(IIIu)

Compounds of general formuls IIb, i.e. compounds of formula II where Z is oxygen, can be converted to teh corresponding compounds IIv where Z is sulfur by reaction with $P_2S_5$. The reaction is shown in Scheme 13.

Scheme 13

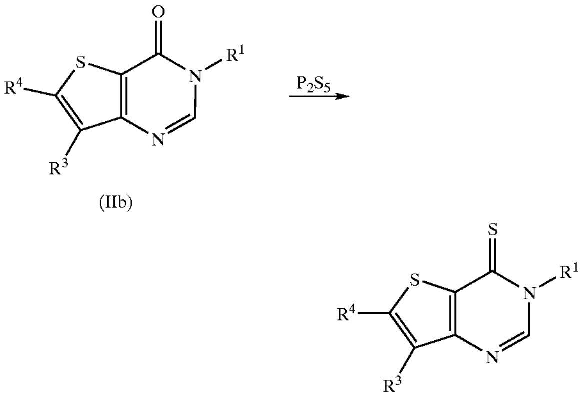

(IIb)

(IIv)

Equivalent compounds of general formula III and IV can be made mutatis mutandis in similar manner.

Other methods will be apparent to the chemist skilled in the art as will be the methods for preparing starting materials and intermediates.

The invention is illustrated in the following Examles. Structures of isolated novel compounds were confirmed by NMR and/or other appropriate analyses.

EXAMPLE 1

6-Bromo-3,4-dihydrothieno[3,2-d]pyrimidin-4-one (compound 8a)

A solution of the product from step c) (0.22 g), hydrobromic acid (2 ml, 46% solution) in glacial acetic acid (10 ml) was heated under reflux for 6 hours. On cooling the mixture was diluted with water and the mixture filtered. The solid was washed with water and air-dried to give the title product, m.p. 238–240° C.

Preparation of Starting Materials a) 4-Chlorothienol[3,2-d]pyrimidin-4-one (compound 8a)

A mixture of compound 1h (see Table H) (10 g) and phosphorous oxychloride (100 ml) was heated under reflux for 5 hours. On cooling, the solution was evaporated to dryness and the residue added to ice-water (with caution). The mixture was extracted with ethyl acetate and then dichloromethane. The organic portions were washed with sodium hydrogen carbonate solution followed by brine, dried ($MgSO_4$) and filtered through a silica pad. The filtrate was evaporated go give the title product.

b) 4-Methoxythieno[3,2-d]pyrimidine

To a suspension of sodium hydride (2 g 60% in oil) in dry dioxane (80 ml) at room temperature was added methanol (6 ml). When effervescence had subsided the product from step a) (5 g) was added and the reaction mixture stirred overnight at room temperature. The mixture was poured into water and extracted with ethyl acetate (×3). The combined organic extracts were washed with brine, dried ($MgSO_4$), filtered and the solvent removed to give the title product, m.p. 92–94° C.

c) 6-Bromo-4-methoxythieno[3,2-d]pyrimidine

To a solution of the production from step b) (0.5 g) in dry tetrahydrofuran (20 ml) was added lithium diisopropylamide (1.53 ml, 2 M) at −78° C. and stirring continued for 45 minutes. A solution of N-bromosuccinimide (0.6 g) in dry tetrahydrofuran (10 ml) was added dropwise at −78° C. and then allowed to attain room temperature over one hour. The reaction mixture was poured into ice-water and extracted with ethyl acetate (×3). The organic extracts were washed with brine, dried ($MgSO_4$), filtered and the solvent removed. The resulting solid was purified by silica gel chromatography eluting with light petroleum (60–80° C.)/ethyl acetate (2:1) to give the title product, m.p. 111–113° C.

EXAMPLE 2

7-Bromo-6-methyl-3,4-dihydrothieno[3,2-d]pyrimidin-4-one (compound 2a)

A stirred solution of compound 7a (see Table A) (2.1 g), bromine (0.2 ml) and glacial acetic acid (2 ml) was heated under reflux for 5 hours. On cooling, the reaction mixture was poured into water. The mixture was then filtered to give a solid which was washed with water and then light petroleum (b.p. 60–80° C.) and dried to give the title product, m.p. 320–322° C.

The following compounds of formula IIa in Table A, i.e. compounds of formula II where Z is oxygen and $R^1$ is hydrogen, may be prepared by one or more methods analogous to those of Examples 1 and 2.

TABLE A (IIa)

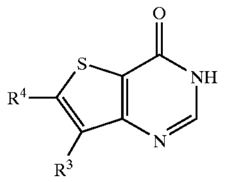

| Cmp | $R^3$ | $R^4$ | m.p./° C. |
|---|---|---|---|
| 1a | Br | H | 330–332 |
| 2a | Br | Me | 320–322 |
| 3a | Cl | H | 298–301 |
| 4a | Cl | Cl | 278–289 |
| 5a | Br | Ph | 329–331 |
| 6a | Br | tBu | 299–301 |
| 7a | H | Me | 201–203 |
| 8a | H | Br | 238–240 |
| 9a | H | vinyl | 84–88 |
| 10a | Me | Br | 246–249 |
| 11a | Br | $Me_3Si$ | 293–296 |

EXAMPLE 3

3,6-Dimethyl-3,4-dihydrothieno[3,2-d]pyrimidin-4-one (compound 19b)

To a stirred suspension of sodium hydride (0.05 g, 60% in oil) in dry N-methylpyrrolidinone (2 ml) at room temperature was added compound 7a (0.1 g) and stirring continued for 15 minutes. Iodomethane (0.1 ml) was then added and stirring continued at room temperature overnight. Water was added and the mixture extracted with ethyl acetate (×3). The organic extracts were combined and dried ($MgSO_4$), filtered through a silica pad and the solvent removed. The residue was triturated with diisopropyl ether to give the title product, m.p. 188–190° C.

The following compounds of formula IIb in Table B, i.e. compounds of formula II where Z is oxygen may be prepared by one or more methods analogous to those of Example 3.

TABLE B (IIb)

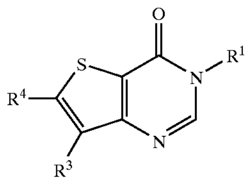

| Cmp | $R^1$ | $R^3$ | $R^4$ | m.p./° C. |
|---|---|---|---|---|
| 1b | Me | Br | H | 212–214 |
| 2b | benzyl | Br | H | 132–134 |
| 3b | allyl | Br | H | 96–98 |
| 4b | iBu | Br | H | 116–118 |

TABLE B-continued (IIb)

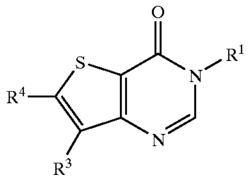

| Cmp | $R^1$ | $R^3$ | $R^4$ | m.p./° C. |
|---|---|---|---|---|
| 5b | 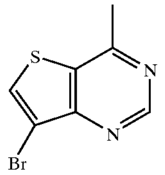 | Br | H | 333–338 |
| 6b | i-Pr | Br | H | 148–150 |
| 7b | 3-PhO-benzyl | Br | H | 117–120 |
| 8b | $2-CF_3$-benzyl | Br | H | 137–139 |
| 9b | 4-Cl-benzyl | Br | H | 162–164 |
| 10b | 2,6-diCl-benzyl | Br | H | 181–183 |
| 11b | 4-MeO-benzyl | Br | H | 159–161 |
| 12b | propargyl | Br | H | 144–146 |
| 13b | 2,4,6-triCl-phenoxyethyl | Br | H | 161–163 |
| 14b | $—CH_2C(=O)OMe$ | Br | H | 170–172 |
| 15b | $—CH_2C(=O)OBut$ | Br | H | 169–171 |
| 16b | $—CH_2C(=O)OH$ | Br | H | 248–250 |
| 17b | Me | H | H | 168–169 |
| 18b | $—CO_2Et$ | Br | H | 126–128 |
| 19b | Me | H | Me | 188–190 |
| 20b | 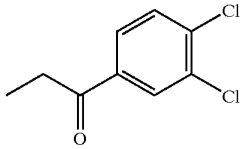 | Br | H | 230–232 |
| 21b | $—CH_2(C=O)Ph$ | Br | H | 195–196 |
| 22b | $—CH_2CN$ | Br | H | 199–201 |
| 23b | 3,4-diCl-benzyl | Br | H | 191–192 |
| 24b | 2-Cl-benzyl | Br | H | 127–131 |
| 25b | 2,4-diCl-benzyl | Br | H | 146–147 |
| 26b | Et | Br | H | 156–159 |
| 27b | 4-Br-benzyl | Br | H | 170–175 |
| 28b | 4-tBu-benzyl | Br | H | 204–207 |
| 29b | 2,4-diCl-benzyl | Me | H | 158–159 |
| 30b | benzyl | Me | H | 126–127 |
| 31b | $2-CF_3$-benzyl | Me | H | 133–134 |
| 32b | 3-PhO-benzyl | Me | H | 98–99 |
| 33b | 2-Cl-benzyl | Me | H | 133–134 |
| 34b | 4-Cl-benzyl | Me | H | 169–170 |
| 35b | 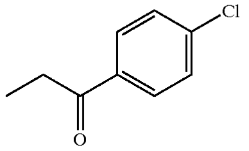 | Me | H | 224–225 |
| 36b | 4-Br-benzyl | Me | H | 166–167 |
| 37b | 3,4-diMeO-benzyl | Me | H | 136–137 |
| 38b | 4-tBu-benzyl | Me | H | 201–202 |
| 39b | 2,4-diMe-benzyl | Br | H | 124–126 |
| 40b | 3,4-diMeO-benzyl | Br | H | 190–193 |

TABLE B-continued (IIb)

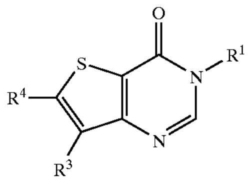

| Cmp | $R^1$ | $R^3$ | $R^4$ | m.p./° C. |
|---|---|---|---|---|
| 41b | 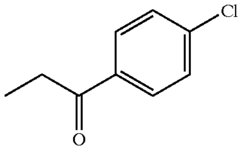 | Br | H | 201–206 |
| 42b | 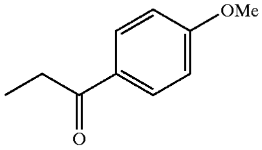 | Br | H | 196–200 |
| 43b | 3-$CF_3$-benzyl | Br | H | 150–152 |
| 44b | —$(CH_2)_2OC(=O)Me$ | Br | H | 123–124 |
| 45b | —CH(Ph)—C(=O)OMe | Br | H | gum |
| 46b | —$CH(CO_2Et)_2$ | Br | H | 92–93 |
| 47b | —$CH(iPr)CO_2Et$ | Br | H | 93–94 |
| 48b | —$CH(Me)CO_2Et$ | Br | H | 122–123 |
| 49b | —$CH(Pr)CO_2Et$ | Br | H | 82–84 |
| 50b | 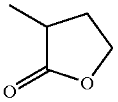 | Br | H | 248–250 |
| 51b | but-2-eneyl | Br | H | 133–134 |
| 52b | —$CH_2C(=O)NH_2$ | Br | H | 277–281 |
| 53b | 3-$NO_2$-benzyl | Br | H | 216–218 |
| 54b | phenylpropyl | Br | H | 81–83 |
| 55b | decyl | Br | H | 50–52 |
| 56b | 4-$NO_2$-phenyl | Br | H | 285–290 |
| 57b | 2,4-diCl-benzyl | Br | tBu | 149–150 |
| 58b | 2-$CF_3$-benzyl | Br | tBu | 172–173 |
| 59b | 3-PhO-benzyl | Br | tBu | 123–124 |
| 60b | 2-Cl-benzyl | Br | tBu | 160–161 |
| 61b | 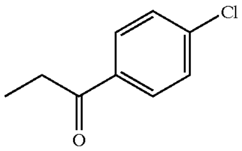 | Br | tBu | 209–210 |
| 62b | 4-Cl-benzyl | Br | tBu | 116–117 |
| 63b | 4-Br-benzyl | Br | tBu | 121–122 |
| 64b | 4-tBu-benzyl | Br | tBu | 172–173 |
| 65b | benzyl | Br | tBu | oil |
| 66b | 3,4-diMeO-benzyl | br | tBu | oil |
| 67b | Me | Br | tBu | 133–134 |
| 68b | Me | Br | Ph | 202–204 |
| 69b | 3-Cl-5-$CF_3$-2-pyridyl | Br | tBu | 202–203 |
| 70b | 3-Ph-1,2,4-thia-diazol-5-yl | Br | H | 270–272 |
| 71b | Me | Me | H | 194–195 |
| 72b | 3-Cl-5-$CF_3$-2-pyridyl | Br | H | 180–183 |
| 73b | Me | —$(CH)_3$—N— | | 236–237 |
| 74b | 2-$NO_2$-4-$CF_3$-phenyl | Br | H | 212–214 |

EXAMPLE 4

7-Bromo-3-hydroxy-3,4-dihydorthieno[3,2-d]pyrimidin-4-one (compound 2c)

A solution of the starting material (1.4 g) and ethyldiisopropylamine (0.65 g) in 1,4-dioxan (20 ml) was heated under reflux for 24 hours. On cooling, the reaction mixture was acidified with dilute hydrochloric acid and water (20 ml) was added. The solution was filtered to give a solid which was washed and dried to give the title product, m.p. 244–247° C.

Preparation of Starting Material a) Methyl 4-bromo-3-(dimethylaminomethylene)amino-2-thenoate A solution of methyl 3-amino-4-bromo-2-thenoic acid (for preparator, see J. Gen. Chem. USSR, (1964), 34, 961) (5 g) and N,N-dimethylformamide dimethyl acetal (5 g) in toluene (30 ml) were heated under reflux for 8 hours. On cooling the solvent was removed and the residue purified by silica gel chromatography eluting with ethyl acetate: light petroleum (b.p. 60–80° C.) (1:3) to give the title compound.

b) Methyl 4-bromo-3-[(hydroxyiminomethyl)amino]-2-thenoate

To a stirred solution of the product from step a) (1.0 g) in methanol (10 ml) was added hydroxylamine hydrochloride (0.47 g) at room temperature. After 10 minutes, stirring was stopped and the mixture allowed to stand at room temperature for 3 hours. The mixture was filtered to give a solid, which was washed with chilled methanol (3 ml) and dried to give the title product.

EXAMPLE 5

7-Bromo-3-(4-methoxy)benzyloxy-3,4-dihydrothieno[3,2-d]pyrimidin-4-one (compound 3c)

To a stirred suspension of sodium hydride (0.053 g, 60% in oil) in dry NMP (5 ml) at room temperature was added the product from Example 4 (0.325 g), and stirring was continued until effervescence ceased. 4-Methoxybenzyl chloride (0.2 g) was then added and the reaction mixture was stirred for 24 hours at room temperature. The reaction mixture was poured into water and the resulting white precipitate was filtered to give a white solid. This white solid was dissolved in dichloromethane and dried ($MgSO_4$). Removal of the solvent gave the title product, m.p. 178–180° C.

EXAMPLE 6

3-Acetoxy-7-bromo-3,4-dihydrothieno[3,2-d]pyrimidin-4-one (compound 4c)

To a solution of acetyl chloride (0.234 g) in dry tetrahydrofuran (3 ml) was added a solution of the product from Example 4 (0.741 g) in pyridine (0.237 g) and N-methylpyrrolidone (5 ml) at room temperature. The solution was stirred at room temperature for 3 days and then poured into water (15 ml). The resulting precipitate was filtered, washed with water and dried to give title product, m.p. 159–162° C.

The following compounds of formula IIx in Table C, i.e. compounds of formula II where Z is oxygen, $R^1$ is $OR^a$, $R^3$ is bromine and $R^4$ is hydrogen, may be prepared by methods analogous to those of Examples 4 to 6.

TABLE C (IIx)

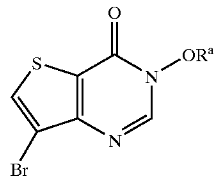

| Cmp | $R^a$ | m.p./° C. |
|---|---|---|
| 1c | Me | 152–154 |
| 2c | H | 244–247 |
| 3c | 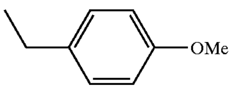 | 178–180 |
| 4c | —C(=O)Me | 159–162 |

EXAMPLE 7

3-Amino-7-bromo-3,4-dihydrothieno[3,2-d]pyrimidin-4-one (compound 6d)

To a stirred solution of the product from step a) Example 4 (1.1 g) in methanol (7 ml) was added hydrazine hydrochloride (0.54 g) and stirring was continued for 1 hour. The reaction mixture was filtered to give a white solid which was washed with water and dried to give the title compound, m.p. 181–183° C.

EXAMPLE 8

3-Acetamido-7-bromo-3,4-dihydrothieno[3,2-d]pyrimidin-4-one (compound 3d)

To a stirred solution of acetyl chloride (0.16 g) in 1,4-dioxan (2 ml) was added a solution of the product from Example 7 (0.5 g) in pyridine (0.16 g) and N-methylpyrrolidinone (0.5 ml) and stirring was continued for 1 hour at room temperature. Water was added and the mixture was filtered to give a solid which was dried to give the title product, m.p. 273° C.

EXAMPLE 9

3-(4-Chlorobenzylidene)amino-7-methyl-3,4-dihydrothieno[3,2-d]pyrimidin-4-one (compound 4d)

A solution of the product from step b (1.6 g), trimethyl orthoformate (10 ml), p-toluene sulfonic acid (catalytic) in xylene (100 ml) was heated under reflux for 2 hours. On cooling the reaction mixture was evaporated to dryness and recrystallised from toluene to give the title product, m.p. 213–215° C.

Preparation of Starting Materials a) 3-Amino-4-methyl-2-thiophenecarbohydrazide

A solution of methyl 3-amino-4-methyl-2-thenoate (25 g) and hydrazine hydrate (20 ml) in butanol (150 ml) was heated under reflux for 18 hours. On cooling the solvent was removed and teh residue was recrystallised from toluene to give the title product, m.p. 141–143° C.

b) $N^2$-(4-chlorobenzylidene)-3-amino-4-methyl-2-thiophenecarbohydrazide

A solution of the product from step a) (3.4 g) and p-chlorobenzaldehyde (2.8 g) in ethanol (200 ml) was heated under reflux for 2 hours. On cooling the reaction mixture was filtered to give the title product.

The following compounds of formula IIy in Table D, i.e. compounds of formula II where Z is oxygen and $R^4$ is hydrogen, may be prepared by one or methods analogous to those of Examples 7 to 9.

TABLE D (IIy)

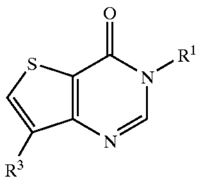

| Cmp | $R^1$ | $R^3$ | m.p./° C. |
|---|---|---|---|
| 1d | —N=CHOMe | H | 120–122 |
| 2d | 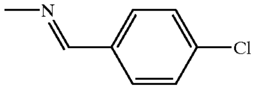 | H | 204–205 |
| 3d | —NHC(=O)Me | Br | 273 |
| 4d | 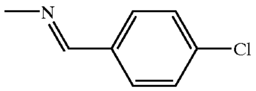 | Me | 213–215 |
| 5d | 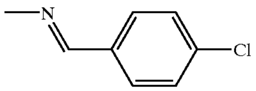 | Br | 235–237 |
| 6d | $NH_2$ | Br | 181–183 |

EXAMPLE 10

7-Bromo-3,4-dihydrothieno[3,2-d]pyrimidin-4-thione (compound 1e)

A solution of 7-bromo-4-chlorothieno[3,2-d]pyrimidine (see below for preparation) (2.0 g), sodium hydrosulfide hydrate (0.66 g) and N-methylpyrrolidinone (10 ml) was heated at 102° C. for 1 hour. Water (500 ml) and ethyl acetate (500 ml) were added and stirred for 1 hour. The layers were separated and the aqueous phase extracted with ethyl acetate (300 ml). The combined organic extracts were washed with brine (300 ml), dried ($MgSO_4$), treated with activated charcoal, then filtered through a silica pad and the solvent removed to give the title product, m.p. 328° C.

Preparation of Starting Materials

7-Bromo-4-chlorothieno[3,2-d]pyrimidine was prepared in analogous fashion to Example 1 step a), starting from compound 1a.

EXAMPLE 11

3,4-Dihydrothieno[3,4-d]pyrimidin-4-one (compound 1f)

A stirred mixture of methyl 4-formamido-3-thenoate (see below) (3.39 g) and ammonium formate (3.4 g) in formamde (5 ml) was heated at 140° C. for 7 hours. On cooling, the mixture was poured into water, and the mixture filtered to give a solid which was washed with water followed by light petroleum (b.p. 60–80° C.) and air dried to give the title product, m.p. 275–278° C.

Preparation of Starting Materials

Methyl 4-formamido-3-thenoate

A stirred solution of methyl 4-amino-3-thenoate (4 g), sodium acetate trihydrate (2.8 g) and formic acid (27 ml) was heated at 95° C. for 1 hour. On cooling the solution was poured into water, and the solution filtered to give the title product as a solid.

EXAMPLE 12

5,7-Dibromo-3,4l-dihydrothieno[3,4-d]pyrimidin-4-one (compound 2f)

A solution of the product from Example 11 (0.9 g) and excess bromine (0.4 ml) in glacial acetic acid (100 ml) were heated at 100° C. for 5 hours until no bromine remained. On cooling the solvent was removed and the residue was dried. The residue was recrystallised from acetic acid to give the title product, m.p. >250° C.

EXAMPLE 13

7-Bromo-3,4-dihydrothieno[3,4-d]pyrimidine-4-one (compound 3f)

A solution of the product from Example 12 (0.9 g) and bromine (0.3 ml) in glacial acetic acid (100 ml) were heated at 100° C. for 2 hours. On cooling the solvent was removed and the residue was dried. The residue was recrystallised from acetic acid to give the title product. m.p. 226–229° C.

EXAMPLE 14

3,4-Dihydrothieno[2,3-d]pyrimidin-4-one (compound 5g)

The product from step b) (4.38 g) and ammonium formate (4.38 g) in formamide (18 ml) was heated with stirring at 150° C. for 7 hours. The mixture was cooled and poured into water. The precipitated solid was filtered, washed with water followed by dichloromethane and dried to give the title product, m.p. 256–8° C.

Preparation of Starting Materials a) Ethyl 2-amino-3-thenoate

Piperidine (20.7 ml) was added dropwise with stirring to a mixture of 2,5-dihydroxy-1,4-dithiane (17.5 g) and ethyl cyanoacetate (23.7 g). The mixture was stirred at room temperature for 4 hours and then allowed to stand overnight. It was filtered and the filtrate evaporated to dryness. The residue was dissolved in ether, filered and evaporated to dryness. The residue was triturated with light petroleum (b.p. 60–80° C.) containing a small amount of ethyl acetate. The gummy solid obtained was purified by silica gel column chromatography and the semi-solid product was triturated with water, filtered and washed with light petroleum (b.p. 60–80° C.) and dried to give the title product.

b) Ethyl 2-formamido-3-thenoate

The product from step a) (14.6 g) was added to a mixture of acetic anhydride (24.3 ml) and formic acid (24.3 ml) with stirring and cooling. The mixture was stirred at room temperature for 4 hours and evaporated under reduced pressure. The residue was dissolved in ether and cooled in dry ice. The precipitate was filtered off and dried to give the title product.

EXAMPLE 15

6-Bromo-3,4-dihydrothieno[2,3-d]pyrimidine-4-one (compound 6g)

The product from Example 14 (0.75 g) was added to glacial acetic acid (10 ml) and heated with stirring until it dissolved. Bromine (0.75 ml) was then added and the mixture immediately set solid. More acetic acid was added and the mixture broken up. It was then heated at 80° C. for 6½ hours, cooled and poured into ice-water. The solid was filtered and washed with water followed by dichloromethane and dried to give the title product, m.p. 304° C.

The following compounds of formula IVz in Table G, i.e. compounds of formula IV where Z is oxygen, may be prepared by one or more methods analogous to those of Examples 3, 14 and 15.

TABLE G (IVz)

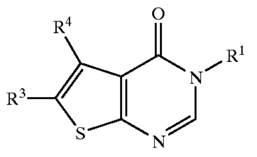

| Cmp | $R^1$ | $R^3$ | $R^4$ | m.p./° C. |
|---|---|---|---|---|
| 1g | H | H | Ph | |
| 2g | Me | H | Me | 132–133 |
| 3g | H | Br | Ph | 271–273 |
| 4g | H | H | Me | 235–237 |
| 5g | H | H | H | 256–258 |
| 6g | H | Br | H | 301–304 |
| 7g | H | H | 2-thienyl | |
| 8g | 3-PhO-benzyl | H | Me | oil |
| 9g | H | Br | Me | 241–243 |
| 10g | 2,4-diCl-benzyl | H | Me | 130–131 |
| 11g | Benzyl | H | Me | 123–124 |
| 12g | 2-$CF_3$-benzyl | H | Me | 106–107 |
| 13g | 2-Cl-benzyl | H | Me | 124–125 |
| 14g | 4-Cl-benzyl | H | Me | 143–144 |
| 15g | 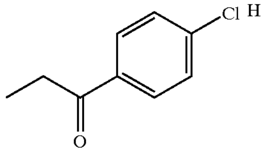 | H | Me | 180–181 |
| 16g | 4-Br-benzyl | H | Me | 155–156 |
| 17g | 3,4-diMeO-benzyl | H | Me | 161–162 |
| 18g | 4-tBu-benzyl | H | Me | 160–161 |

The following compounds of formula IIa in Table H, i.e. compounds of formula II where Z is oxygen and $R^1$ is hydrogen, may be prepared by methods analogous to those of Example 14 replacing ethyl 2-amino-3-thenoate in step a) with the corresponding 3-amino-2-thenoate.

TABLE H (IIa)

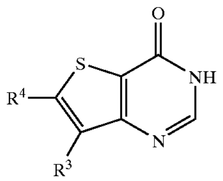

| Cmp | $R^3$ | $R^4$ | m.p./° C. |
|---|---|---|---|
| 1h | H | H | 228–230 |
| 2h | Me | H | 243–246 |
| 3h | | $—(CH)_3N—$ | 340–342 |
| 4h | H | Ph | 271–273 |
| 5h | H | tBu | 235–237 |

TABLE H-continued (IIa)

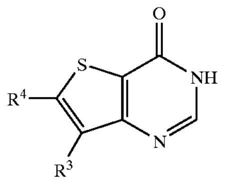

| Cmp | $R^3$ | $R^4$ | m.p./° C. |
|---|---|---|---|
| 6h | Ph | H | 235–237 |
| 7h | H | 4-Cl-phenyl | |
| 8h | Ph | $CF_3$ | |
| 9h | H | 4-F-phenyl | |

Test Example

Compounds were assessed for activity against one or more of the following:

*Erysiphe graminis* f sp. *tritici:* wheat powdery mildew

*Phytophthora infestans:* late tomato blight

*Pyricularia oryzae:* rice blast

*Leptosphaeria nodorum:* glume blotch

*Plasmopara viticola:* downy mildew of vines

Aqueous solutions or dispersions of the compounds at the desired concentration, including a wetting agent, were applied by spray or by drenching the stem base of the test plants, as appropriate. After a given time, plants or plant parts were inoculated with appropriate test pathogens and kept under controlled environmental conditions suitable for maintaining plant growth and development of the disease. After an appropriate time, the degree of infection of the affected part of the plant was visually estimated. Compounds are assessed on a score of 1 to 3 where 1 is little or no control, 2 is moderate control and 3 is good to total control. At a concentration of 500 ppm (w/v) or less, the following compounds scored 2 or more against the fungi specified.

*Erysiphe graminis* f sp. *tritici*

3a, 12a, 1b, 5b, 6b, 7b, 8b, 9b, 10b, 11b, 13b, 14b, 16b, 24b, 25b, 26b, 27b, 41b, 43b, 45b, 47b, 50b, 52b, 53b, 54b, 55b, 61b, 66b, 2f, 3f and 5g.

*Phytophthora infestans*

1a, 8a, 14b, 15b, 2d, 3f and 9h.

*Pyricularia oryzae*

1a, 3a, 4a, 6a, 8a, 10a, 12a, 1b, 4b, 5b, 6b, 7b, 8b, 9b, 10b, 11b, 18b, 20b, 21b, 22b, 25b, 26b, 27b, 30b, 40b, 41b, 43b, 44b, 45b, 46b, 47b, 48b, 49b, 50b, 51b, 52b, 54b, 55b, 57b, 63b, 65b, 66b, 2c, 2d, 6d, 1e, 4g, 5g, 6g, 8g, 9g, 17g, 18g, 1h and 2h.

*Leptosphaeria nodorum*

2b, 5b, 6b, 7b, 9b, 10b, 11b, 13b, 18b, 28b, 29b, 33b, 39b, 41b, 43b, 51b, 1f, 6g, 8g, 4h and 8h.

*Plasmopara viticola*

1b, 5b, 12b, 14b, 15b, 18b, 20b, 21b, 22b, 23b, 28b, 40b, 41b, 1f, 2f, 3f and 10 g.

What is claimed is:

1. 7-Bromo-3-methyl-3,4-dihydrothieno[3,2-d]pyrimidin-4-one.

* * * * *

UNITED STATES PATENT AND TRADEMARK OFFICE
CERTIFICATE OF CORRECTION

PATENT NO. : 6,541,630 B1
DATED : April 1, 2003
INVENTOR(S) : Atherall et al.

It is certified that error appears in the above-identified patent and that said Letters Patent is hereby corrected as shown below:

Title page,
Item [63], Related U.S. Application Data, replace the present paragraph with:

-- [62] Division of application No. 09/423,135, filed Nov. 5, 1999, now Pat. No. 6,432,964, which is a 35 U.S.C. §371 conversion of PCT/GB98/01286, filed May 1, 1998. --

Column 1,
Line 11, "filed" should read -- issued --.

Signed and Sealed this

Ninth Day of September, 2003

JAMES E. ROGAN
*Director of the United States Patent and Trademark Office*